United States Patent [19]

Clarke et al.

[11] 4,415,085

[45] Nov. 15, 1983

[54] DRY PHARMACEUTICAL SYSTEM

[75] Inventors: John W. Clarke, Indianapolis; Dale C. Harris, Fairland, both of Ind.

[73] Assignee: Eli Lilly and Company, Indianapolis, Ind.

[21] Appl. No.: 332,495

[22] Filed: Dec. 21, 1981

[51] Int. Cl.³ ................... B65D 85/62; B65B 57/02; B65B 67/12; B65D 1/02

[52] U.S. Cl. .................................. 206/526; 150/55; 383/9; 383/80; 53/390; 53/281; 206/499; 220/23.2; 211/76; 211/84; 222/107

[58] Field of Search ............... 206/526, 499; 220/23.2; 229/62, 65; 150/0.5; 53/390, 281; 211/76, 84

[56] References Cited

U.S. PATENT DOCUMENTS

| | | | |
|---|---|---|---|
| 3,427,646 | 2/1969 | Scholle | 53/281 |
| 3,437,117 | 4/1969 | Vitello et al. | 229/65 |
| 3,596,430 | 8/1971 | Parish | 206/499 |
| 3,730,738 | 5/1973 | Cook et al. | 229/62 |
| 4,049,033 | 9/1977 | Ralston, Jr. | 222/107 |
| 4,126,223 | 11/1978 | Griffin | 206/526 |

Primary Examiner—William T. Dixson, Jr.
Attorney, Agent, or Firm—Barnes & Thornburg

[57] ABSTRACT

A system for the packaging, shipment, storage, and reconstitution of dry pharmaceuticals includes a flexible bag manufactured from two layers of plastic laminated film and a rigid port-forming member. In the system, the package is used for shipment and storage of dry pharmaceuticals and for their reconstitution in a liquid solution and their intravenous administration. A plurality of such packages may be handled as an assembly by flexible plastic strips both during processing and packaging and during the reconstitution of the dry medicine as a liquid solution. The flexible plastic strips are formed with a plurality of cavities. Each cavity of the strip has a plurality of sites located in its central portion and adapted to engage and retain the port-forming member and to protect its opening from contamination. A plurality of such package assemblies can be enclosed within an outer protective bag to provide protection against moisture and the effects of the environment during shipment and storage. The assemblies may be removed from the outer protective bag by the batching strips and placed in a special rack for support. With a plurality of packages supported by the rack, a hospital pharmacist, using a power-operated pump, may fill each container with a controlled quantity of a liquid solute for the dry pharmaceutical. When the dry medicine is in solution, it may be intravenously administered directly from the package.

29 Claims, 13 Drawing Figures

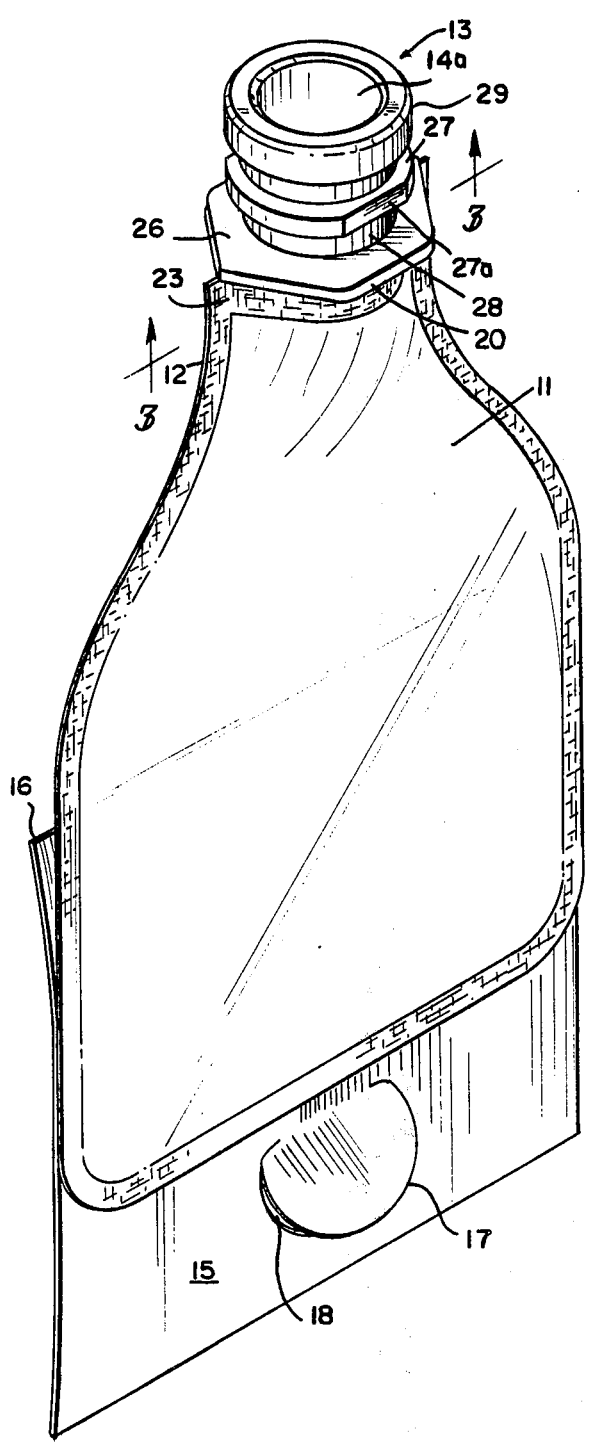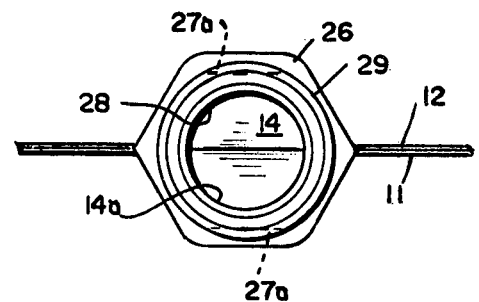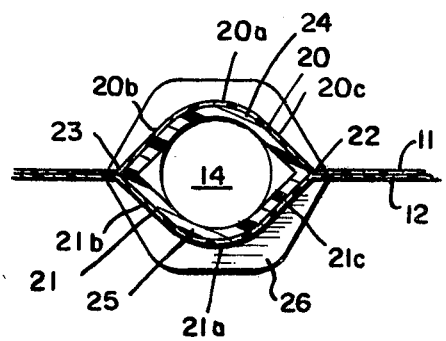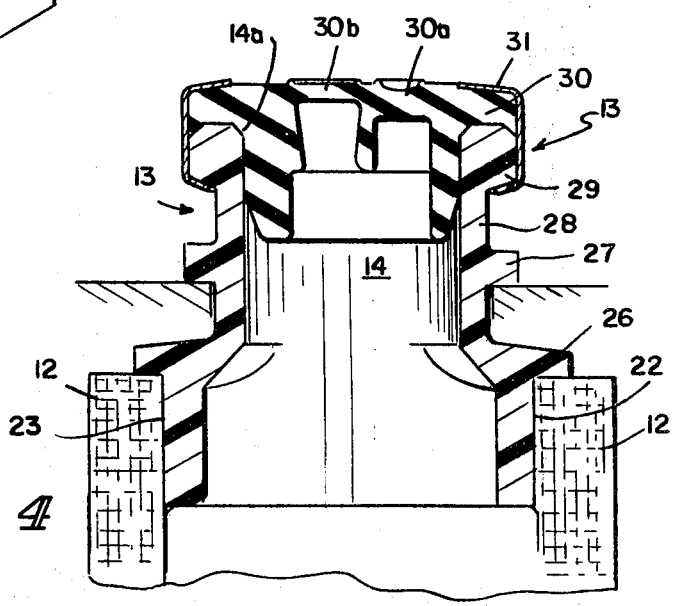

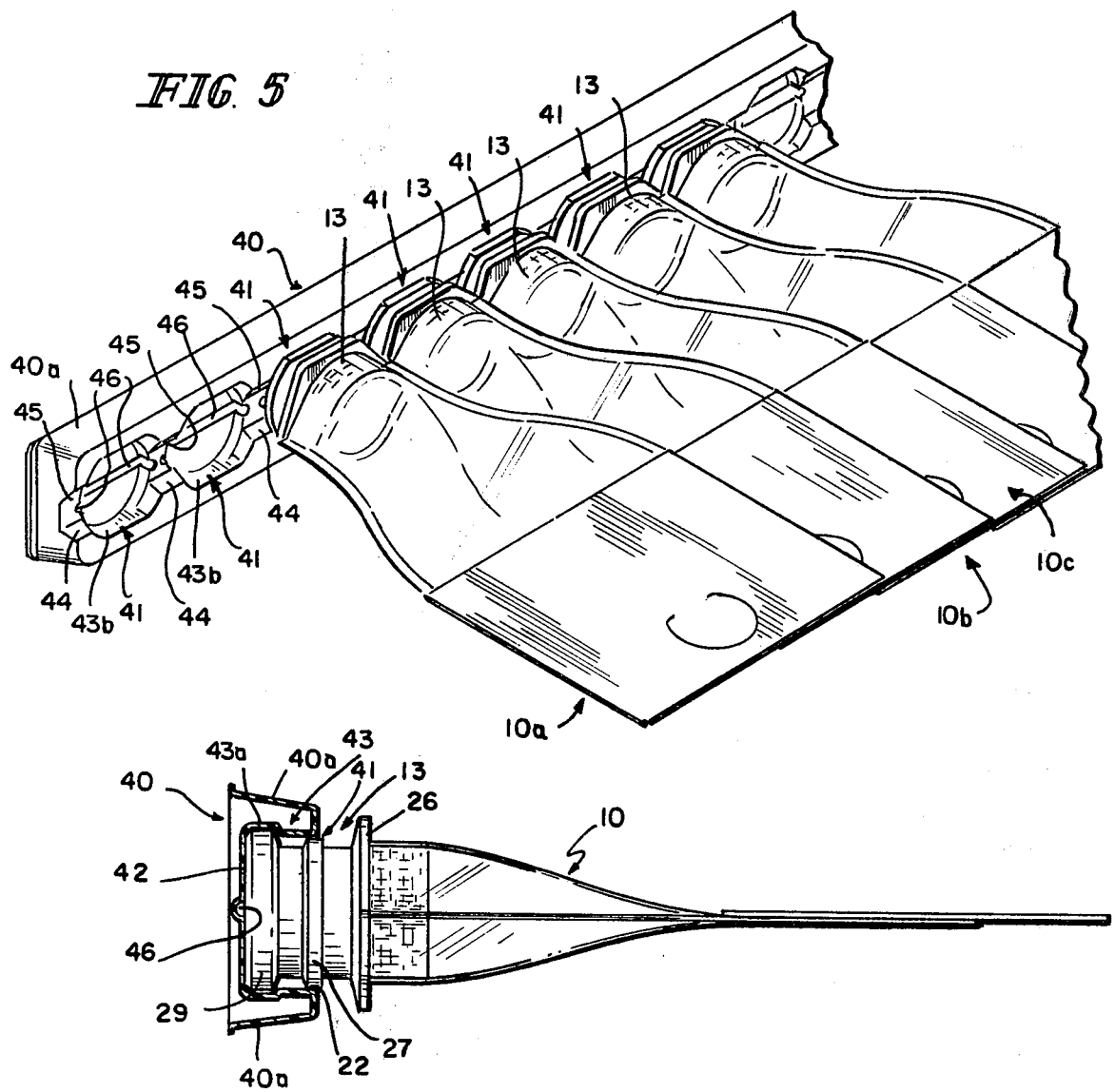

DRY PHARMACEUTICAL SYSTEM

This invention relates to a new system to package, store, ship, and prepare dry medicines for intravenous administration.

Medical treatment frequently requires the administration of fluids and medication solutions intravenously. Such solutions have been packaged in both glass and flexible plastic containers. The solution containers are adapted to be punctured at one end with an IV administration set and to be hung from the other end so that their liquid contents may be removed and infused in the vein of a patient. Where glass containers are used, it is necessary to vent the interior of the rigid glass container to atmosphere to avoid the creation of a pressure differential within the container that prevents it from being emptied. Venting has not been required where plastic film containers are used because the flexibility of their walls prevents any significant pressure differential and permits the container to be emptied.

Some medicines are manufactured and packaged in dry form because their stability is impaired in liquid solutions. Antibiotics are frequently manufactured and packaged for storage and shipment in dry form because of their instability in liquid solution. In the past, such dry medicines have been packaged in glass vials for shipment and storage prior to use.

Where dry medicines have been administered intravenously in the past, liquid solutions of the dry medicines have been prepared shortly before their administration is commenced. Liquid solutions of such dry medicines must be carefully prepared to maintain the sterility of the medicine and to avoid the injection of small particles of medicine into the veins of the patient. Small particles of dry medicine can irritate the patient's vein, causing discomfort.

In hospital treatment, this has meant that the liquid medicine solutions have been prepared from dry medicines at the hospital pharmacy for use by those personnel responsible for their administration. Many different procedures are used by pharmacists in the hospital to prepare liquid solutions, but these procedures have generally required many time-consuming and wasteful steps.

Since dry medicines are most frequently packaged in measured small dosages, such as one-half to two grams, it has frequently been necessary for the hospital pharmacists to store and handle large quantitites of both small glass vials and large administration containers. Preparation of the medicine solution takes place under sterile conditions, and the hospital pharmacist frequently uses batch processing, that is, the reconstitution of many vials of dry medicine at one time, in order to minimize the time invested in each dosage. In preparing such packaged dry medicines for intravenous administration, the pharmacist generally uses an automatic refill syringe to inject quantities of liquid solute into the small glass vials to dissolve the medicine and uses another large syringe to withdraw the dissolved dosages from the small vials and add them to the large administration containers in carefully proportioned amounts. The procedure requires great care by the pharmacist to provide accurate dosages in each of the administration containers. Such procedures also require swabbing of the container closures prior to each entry with the hypodermic needle of the syringe. In addition, frequent changing of hypodermic needles is necessary because the needles become dull in use and may "core" the closures upon entry, thus destroying the ability of the closure to seal the containers.

Pharmaceutical manufacturers have also packaged dry medicines in larger glass bottles with volumes of, for example, 100 to 200 milliliters in which the dry medicine is reconstituted and from which the resulting medicine solution is administered. Use of such glass containers has required venting both during reconstitution and administration. Storage of the large medicine containers requires a large storage space.

Upon preparation, those medicine containers which are not immediately used are either refrigerated or frozen to avoid loss of the effectiveness of the medication during the time they must be stored prior to use. Since refrigerated space is limited, it is particularly disadvantageous to use rigid glass containers and particularly the large glass bottles.

These procedures consumed the pharmacist's time and required tiring manual effort. They also consumed the limited refrigerated hospital storage space, hypodermic needles, and swabbing materials and aggravated the hospital's waste disposal and inventory control problems.

This invention provides a closed unit-dose system and a new dry medicine package in which the dry medicine can be shipped, stored, and more easily reconstituted and from which the dry medicine solution can be more easily administered directly to a patient. The invention facilitates the sterile handling of the package before and after it is filled with dry medicine and materially reduces the materials used and the time and effort of the hospital pharmacist in reconstituting the dry medicine within the container and of the hospital staff in administering the medicine solution to the patient.

The package of the invention is a flexible bag manufactured from two layers of plastic film sealed at one end to a port-forming member and at their periphery to form a container. The port-forming member includes two elongated planar side panels at one end adapted for sealing engagement with the plastic film and includes a large central opening providing a mouth and access to the interior of the container. Around the opening of the port-forming member are two projections, one projection being located adjacent the planar side panels of the member and the second projection being spaced from and located above the first projection. The two projections provide surfaces for supporting the container during processing, handling and reconstitution of the dry medicine. The package provides a container for dry medicine that can be sterilized and handled easily under sterile conditions during its filling and during reconstitution of the dry medicine by the hospital pharmacist.

The system is adapted to permit pluralities of the bag containers to be handled during both the manufacturing process and their use in the hospital pharmacy. The system includes flexible plastic strips and pluralities of the bag containers that are interengaged to permit handling of the containers in groups or batches. The port-forming members of the containers and the flexible plastic strips, at a plurality of sites in their central portions, are adapted to interengage so that a plurality of bag containers can be retained in the plastic strips.

During processing of the empty package, it is handled with the use of an elongated flexible carrier strip. The processing carrier strip has a plurality of depressions spaced centrally along its length. Each depression can be adapted at its side wall to engage and retain the port-forming member of a container, and each depression has a closed end wall. The carrier strip includes depressed surfaces between the side walls of each depression which form a longitudinal channel from one end of the elongated strip to the other. Each depression further includes a narrow channel-forming portion in its closed end wall and in its side walls where they are interrupted by the longitudinal channel of the strip. The elongated flexible strip can engage, frictionally or othewise as described, the port-forming member of a plurality of bag containers, permit group or batch handling of the containers, and protect the mouth of the bag from the entry of contaminant during handling.

The flexible strip through the longitudinal channel and channel-forming portion of each depression permits the interior of the bag to be sterilized with a sterilizing gas, for example, ethyleneoxide gas. In order to facilitate processing, a port-forming member may be provided with two projecting upper rings in addition to the projection adjacent its planar side panels. The uppermost ring may surround the mouth of the container and the second ring of the port-forming member may include an asymmetrical portion. The depressions of the elongated flexible strip may be deep and may include, in a portion of their side walls, a mating asymmetrical portion for preventing the containers from rotating within the flexible strip during processing. The uppermost ring may, through the flexibility of the plastic strip, be urged past the asymmetrical portion of the plastic strip. This arrangement captures the bag in the strip and removes the need for a frictional interfitting of the strip and bag container. Upon the completion of sterilization, the flexible carrier strip prevents contamination of the sterilized bag and protects the opening during handling until such time as it is filled with dry medicine and sealed.

After the bag containers have been filled with dry medicine, they can be sealed by a conventional elastomeric closure that is fastened in place in the mouth of the container, and another elongated flexible carrier strip is provided to carry a plurality of packages of dry medicine in groups or batches as a container assembly.

The batching carrier strips for the containers of dry medicine may also be formed from elongated flexible plastic strips having a plurality of depressions spaced centrally along their length. Each depression will have a closed end wall and can have side walls adapted to be frictionally engageable with the containers adjacent their mouth. The elastomeric closure may, for example, be sealed to the package with a crimped aluminum band in the conventional manner, and the depression side walls can engage the metal band. The end walls of the depressions are closed and a plurality of the sterile dry medicine bags can be handled without contamination of the closure. The central portion of the carrier strip can be further depressed so that it does not contact the enclosed end of the container.

A plurality of container assemblies each with a plurality of containers of dry medicine can be nested together, and the multiplicity of container assemblies can be further packaged within a storing and shipping container that provides a moisture barrier to enhance the storage life of the medicine and to assist the individual bag containers in providing such moisture barrier protection. The storing and shipping container may be a bag made of a composite metal foil-polyolefin film laminate which can be sealed to provide a moisture barrier for the contained dry medicine bags. The containers of dry medicine can be thus shipped and stored in plural assemblies within such a protective outer bag.

The system of the invention can also assist the hospital pharmacist in the preparation of liquid dosages of such dry medicines. The system includes a pharmacy rack for use in reconstitution of the dry medicines. The rack includes an upper portion forming an elongated slot and a lower portion forming a base. With the rack resting on its base, the upper portion is supported generally horizontal and several inches above the base and provides an obstruction-free access to the elongated slot.

In reconstituting the dry pharmaceuticals, the pharmacist can thus remove from storage one or more storing and shipping containers, each with a multiplicity of dry medicine container assembles. Upon opening the outer protective bag, the pharmacist can remove the dry medicine containers from the protective bag in pre-arranged groups by their carrier strips and place an entire group within the pharmacy rack by sliding a projection of the port-forming members of the bags over the upper portions of the pharmacy rack that form the elongated slot. The flexible carrier strip can then be removed, exposing the closure of each bag. The pharmacy rack has a largely open structure, i.e., it is without surfaces which block the flow of sterile air sweeping the work area. The plurality of bags can be thus supported and held under sterile conditions on the pharmacy rack while the dry medicine within the bags is being reconstituted.

The system also includes a pump capable of delivering controlled quantities of fluid. This pump materially assists the hospital pharmacist in preparing liquid doses of the dry medicine and releases him from the tiring manual use of a syringe to place a solution for the dry medicine within the package.

Thus with the system, a dry medicine reconstitution procedure followed by the pharmacist will include removal of the flexible batching carrier strip for the dry medicine bags within a sterile environment, swabbing of the closures with alcohol to ensure their sterility, and pumping of measured quantities of solute within the packages while they are supported on the pharmacy racks. When once filled, the flexible bags can be either agitated or can be kneaded and deformed to assist placing the dry medicine in solution.

Once the medicine is in solution, the dry medicine solution may be administered to the patient directly from its flexible bag package through the use of a standard non-vented IV administration set, or the medicine solution may be administered piggy-back with other solutions in a manner which is common hospital practice.

The invention thus provides a closed unit-dose system. Other features of this invention will be apparent from the drawings and description which follow.

FIG. 1 is a perspective view of the package of this invention;

FIG. 2 is a partial view from above the package of FIG. 1 showing the mouth of the container;

FIG. 3 is a view along section 3—3 of FIG. 1;

FIG. 4 is a cross-sectional view of the port-forming member of the container of FIG. 1 with its closure in place;

FIG. 5 is a perspective view of the processing carrier strip and containers;

FIG. 6 is a cross-sectional view of the processing carrier strip taken along line 6—6 to show its engagement with the package (which is not sectioned);

Figure 7:
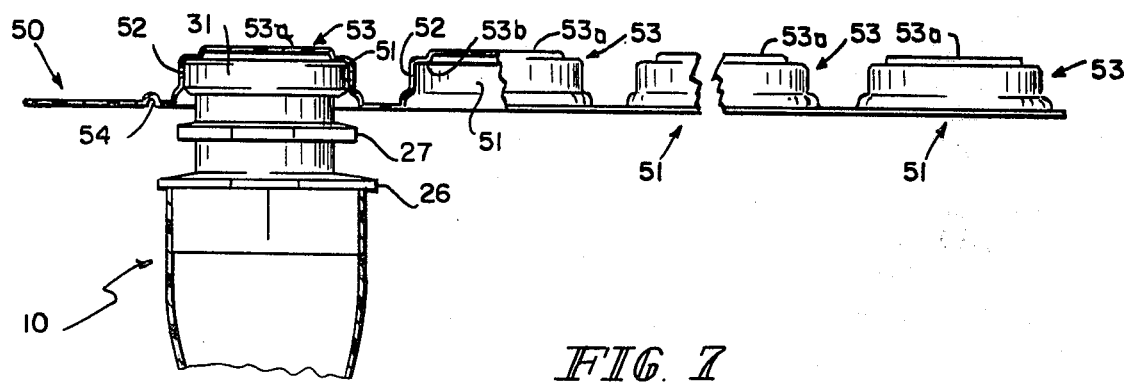
FIG. 7 is a partial cross-sectional view of the batching carrier strip for the sealed packages showing the manner of its engagement with one of the containers.

FIG. 1 illustrates a flexible package 10 of this invention for use with dry medicine. The package consists of two sheets of flexible film 11 and 12 forming its side walls (see also FIGS. 2 and 3), and a port-forming member 13. The flexible side walls 11 and 12 are preferably made from a composite plastic film laminate sold by the Minnesota Mining and Manufacturing Company under the trademark SCOTCH-PACK #8. The SCOTCH-PACK #8 film is a preformed polyester film onto which a polyethylene resin has been extruded. The polyester film, which is oriented to form the outside of the bag-like container, is composed of terephthalic acid and ethylene glycol. No significant adhesives or primers or any other chemical agents form the laminate. The polyethylene film is of medium density and contains no lubricant, slip agents, or anti-block agents, or any other monomeric substance other than polyethylene and is inert to the medicine contained in the package. The preferable film consists of a layer of polyester film 0.0005 inch thick with a medium density polyethylene film of 0.0015 inch. Prior uses of SCOTCH-PACK #8 film have included boilable food containers for home use. The port-forming member 13 is preferably injection-molded from polyethylene resins sold by the Du Pont Company under their trademark ALATHON #7240.

The two sheets of film 11 and 12 are sealed at their peripheries and to one end of the port-forming member 13, as shown in FIG. 3, to form a container between the central unsealed portions of the two sheets 11 and 12. The port-forming member 13 has a large central bore 14 forming the mouth 14a of the flexible bag container 10. At the end of the bag container opposite its mouth, the two layers of flexible film may be sealed together by their polyethylene layers to form a rectangular panel 15. A label 16 may be affixed to the panel 15 to carry identifying information regarding the medicine and the dosage enclosed within the package and directions for its use. A rectangular panel 15 may be cut in its central portion along the line 17 to provide an opening 18 to permit it to be hung upside down.

The port-forming member 13 is adapted at the end opposite its mouth 14a for insertion between and sealing engagement with the two layers of film 11 and 12. As shown in FIG. 1, the end of member 13 defines two elongated side panels 20 and 21 (see FIG. 3) to which two layers of plastic film 11 and 12, respectively, are sealed. The elongated panels 20 and 21 as shown in FIG. 3 meet on opposite sides of the bore 14 at a plane through its central axis, forming vertices 21 and 23 with included angles of, preferably, about 90°. Each panel has a curved center portion 20a and 21a, respectively, generally concentric with the central axis of bore 14 with ends, 20b, 20c and 21b, 21c, respectively, extending in a straight line tangentially from their center portions to their intersection at the vertices 22 and 23. The bag-engaging end of member 13 thus generally resembles the simplified outline of a human eye as shown in FIG. 3. This structure permits a central bore having a relatively large inner diameter which facilitates filling the package with dry powder-like medicine. In addition, the panels 20 and 21 provide a large planar area to which the layers of film 11 and 12 may be easily adhered. Further, the intersection of panels 20 and 21 with an included angle of about 90° provides a conformation of material at the vertices 22 and 23 as layers 11 and 12 are affixed and precludes the formation of voids at the vertices 22 and 23 in the finished bag. For example, where member 13 provides a central opening of 0.72 inch and the thickness of the end portions 24 and 25 of member 13 forming the elongated panels is 0.08 inch and the height of each panel is 0.44 inch, over one square inch is available on each of the elongated panels 20 and 21 to which films 11 and 12 may be adhered.

The empty package is preferably manufactured in a clean room facility and may be manufactured in a continuous process. For example, two rolls of film may be mounted and unrolled to place the two layers of film adjacent. The two layers of film can be treated to eliminate static charges and the polyethylene side can be cleaned with vacuum prior to the first sealing operation. The adjacent layers can then be punched to provide indexing holes between each of the containers to be formed. The first subsequent step of formation can be to heat seal the two layers of polyethylene film together to form the bottom and sides of a bag container and to form a necked opening at one end. At this step, the bag can also be die-cut to form its ultimate shape. In the second subsequent operation, the edge of the film can be notched to form the opening into which port-forming member 13 is to be inserted and the hole at the end of the container opposite the mouth can be scrapped. In the next step, a port-forming member 13, which is carried by a moving pin, can be inserted into the notched opening of the bag. In the fourth subsequent step of manufacture, heat and pressure can be applied between the film layers 11 and 12 and port-forming member 13 at panels 20 and 21 to seal the port-forming member into the container. Finally, the film of the container can be scrapped; and finished bags can be inserted into a carriage rail, and the pin that has carried the port-forming member 13 retracted. Upon completion of each of the bags, it may be pressured-tested for leaks. The completed empty containers are then assembled by the rail in groups, for example, of ten.

In a typical bag container of this invention, the sealed portion at the periphery of the bag will be about 0.1875 inch wide. The length of the enclosure portion of the bag may have a depth on the order of 5¼ inches and a width at its widest point of 3⅜ inches. The end of the flexible bag adjacent the port-forming member 13 includes portions which taper towards the mouth 14a at an angle on the order of 30°. This permits a flow of material from within the container to be delivered to the mouth of the container without pockets in which it may be trapped and permits the dosage within the container to be substantially entirely removed. Where a planar panel 15 is provided at the end of the bag, it may, for example, have a width of 1¼ inches to provide a panel 1¼ inches by 4 inches to which an information card or label 16 may be affixed. The hanger hole 18 may be of any convenient size or shape and is preferably die-cut into the panel 15 and information card 16 after the information card 16 has been sealed in place on the empty container.

The typical bag described above is designed for ½ to 2 grams dose and up to 100 milliliters of liquid solution.

In the system of this invention, the port-forming member 13 is adapted to permit sterile handling and packaging of the dry medicine and batch processing of the package, both when empty and in preparation and administration of the medicine solution. The mouth-forming portion of member 13 thus has two portions 26 and 27 that project from its generally cylindrical body 28 (see FIG. 1 and FIG. 3). The first projecting portion 26 is adjacent the planar panels 20 and 21. The second projecting portion 27 projects from member 13 intermediate the first portion 26 and the mouth 14a of the port-forming member 13. This can be more readily seen in FIG. 4.

In the preferred embodiment shown, the first projection 26 is generally in the form of a hexagon that extends from the cylindrical body 28 of member 13. The hexagonal projection 26 can have a width of 1.250 inches across the flats and of 1.430 inches from vertex to vertex. The second projection 27 can be in the form of an annular ring that projects from the cylindrical body 28, beginning at a point about 0.33 inch above the lowermost surface of projection 26, and can have a height on the order of 0.08 inch. The uppermost surface of hexagonal portion 26 can project from the cylindrical body 28 of member 13 typically 0.13 inch from its lowermost surface. The first projection 26 and second projection 27 thus form upper and lower surfaces, respectively, that are separated and spaced about 0.20 inch. The bag can also have a projecting annular ring 29 at the mouth 14a of member 13 with a height, for example, of 0.21 inch from the uppermost surface of member 13 to the junction of ring 29 with the cylindrical body 28. The annular rings 27 and 29 can project from the cylindrical body 28 about 1/10 of an inch. The second annular ring 27 may have an asymmetrical portion 27a such as the flat shown in FIG. 1 or may have two asymmetrical flats such as those shown in phantom lines in FIG. 2. Thus, the overall height of member 13 may be on the order of 1¼ inches.

The projections 26 and 27 provide surfaces by which the bag can be carried and from which the bag can be supported in handling during its manufacture, its sterilization, its filling, it packaging, and during the reconstitution of its dry medicine into solution form and during administration and storage after it is reconstituted. The first projection 26 specifically provides surfaces: (1) to permit removal of a carrier strip by providing an uppermost surface that can be gripped and pulled against; (2) to protect the most fragile portion of the seal at the vertices 22 and 23 of the lower portion of member 13; and (3) to permit, easily, the insertion of an IV administration set by hospital personnel.

The flexible container for dry medicine 10 after it has been sterilized and filled may be sealed as shown in the cross-sectional view of FIG. 4. An elastomeric stopper 30 can be inserted into the bore 14 and seated on the mouth-forming portion of member 13. The projecting annular ring 29 can assist in seating the closure 30 on the uppermost surface of member 13. The closure 30 can be compressed and sealed into the mouth, for example, by an annular metallic ring 31 which may be made of any thin metal, typically aluminum, that may be crimped under the annular ring 29. The use of an elastomeric closure 30 and an annular metallic ring 31 is well known in the packaging of pharmaceuticals.

The closure 30 includes two portions. The first portion 30a is thicker than the second portion 30b and is adapted to provide a site for entry of a hypodermic syringe (to permit solution to be placed within the container to dissolve the dry medicine) and, through its thickened portion, to seal the rupture made by the hypodermic syringe upon extraction of the hypodermic syringe. The portion 30b is thinner and provides a site for the insertion of an intravenous administration set. Since site 30b is only used once and since the intravenous administration set generally includes a relatively blunt plastic spike and is used only once, the thinner portion 30b contributes to the ease of use and provides adequate sealing engagement with the standard intravenous administration set.

Such an elastomeric closure 30 may be manufactured from rubber. The portion 30a may have a thickness on the order of 1/10 of an inch, and the portion 30b may have a thickness on the order of 1/20 of an inch. The upper surface of the closure 30 is preferably marked with indicia locating portions 30a and 30b and labelling them approximately for identification and use by the hospital staff.

The member 13 of container 10 is also adapted to interact with flexible carrier strips to permit a plurality of such containers to be conveniently handled during processing, packaging, shipment, and in reconstitution of the dry medicine in solution form as shown in FIGS. 5–8 and 11.

FIG. 5 shows a plurality of bag containers of this invention carried by an elongated flexible strip for handling the empty bag containers during processing. The plurality of empty containers 10a, 10b, 10c, etc., are carried by a processing carrier strip 40. The carrier strip is typically manufactured by thermoforming it from a plastic strip of natural styrene approximately 0.015 inch in thickness. The carrier strip includes a plurality of cavities or depressions 41 spaced centrally along its length. Each depression 41 is formed by a closed end wall 42 and a side wall 43. The processing carrier strip 40 includes a plurality of additional depressed surfaces 44 and 45 between each of the depressions 41 which form a longitudinal channel from one end of the carrier strip 40 to the other, intersecting the plurality of depressions at their side walls 43. Each depression 41 of the processing carrier strip 40 also includes a narrow channel-forming portion 46 in its end wall 42 and its side wall 43 as shown in FIGS. 5 and 6. The channel-forming portion 46 in each of the side walls 43 is located between depressed surfaces 44 and 45 and thus within the interruption of the depressions 41 by the longitudinal channel formed centrally within the carrier strip.

As shown in FIG. 6, the side wall 43 of each depression 41 can include a first cylindrical portion 43a adjacent its closed end 42 and a second portion 43b which may be asymmetrical with a single straight-line portion or, as shown in FIG. 5, may be formed with two straight-line side wall portions (still referred to as the asymmetrical portion for brevity). The depressions 41 are adapted to engage port-forming members 13 of the containers 10, as shown in FIGS. 5 and 6. As indicated above, the second projecting ring 27 of member 13 may include a single asymmetrical portion 22 or two non-round portions as shown which, upon insertion of the member 13 into a depression 41, mates the asymmetrical portion 43b of the depression 41, thereby orienting and preventing the rotation of the container 10 in the processing carrier strip 40. As shown in FIG. 6, upon insertion of member 13 into the depression 41, the annular ring 29 may be urged past the asymmetrical portions 43b of strip 40 because of the strip's flexibility and become captive within portion 43a when the strip 40 resumes its original shape without frictional engagement between member 13 and strip 40. This permits the strip 40 to carry the containers and facilitates exposure of the container interior to sterilizing gas, as described below.

In order to provide a measure of rigidity to the elongated carrier strip 40, it can include side wall portions 40a at its periphery extending in the direction of and about the outer side wall surfaces of the plurality of depressions 41 as shown in FIG. 6.

The carrier strip is thus adapted to carry a plurality of containers 10 during processing. The mouth of the container is protected by the processing carrier strip 40 against the introduction of spurious particulate matter. Furthermore, the channel-forming portions 46 of each depression 41 and the elongated channel formed by the plurality of surfaces 44 and 45 along the axis of the strip permit the interior of each container to be exposed to atmosphere. During processing, the carrier strips 40 each carry a plurality of containers 10, and the interior enclosures of the containers 10 can be exposed to ethylene oxide gas which is permitted to flow into the containers 10 through the channels formed by the surfaces 44, 45, and 46 of the elongated strip 40 and sterilize the interior surfaces of the package which will contact the dry medicine.

The system thus permits convenient handling during processing, prevents the introduction of spurious contaminants, and permits the containers to be sterilized by treatment with ethylene oxide gas.

The processing carrier strips 40 further permit the bags to be handled in groups and introduced into a continuous production line to fill and finish the container. In such further processing, the containers 10 are supported by the lowermost surface of projection 27. The flexible strips 40 are removed after the assemblies of strips 40 and bags 10 are placed on the conveying apparatus; and the individual bags are conveyed while supported by projection 27, one after the other, past a filling machine which introduces into each container a measured dosage of dry medicine. The open port 14 of each container permits the bags to be readily filled with the dry particulate medicine through the use of the filling machinery. After each bag is filled, it is provided with a closure 30 which is then sealed in member 13 of the package. The system also permits the use of standard machinery to place an elastomeric closure within each container and to seal it, for example, with the metallic ring-like band, as shown in FIG. 4.

In this system, upon completion of the finishing operations, the port-forming members 13 of the containers 10 are placed in engagement with a batching carrier strip 50 in groups of, for example, six. FIG. 7 shows such a batching carrier strip and the manner in which it engages the filled and closed container. The carrier strip 50 is thermoformed from natural styrene having a thickness of 0.15 inch. The carrier strip comprises an elongated flexible plastic strip 50 having a plurality of depressions 51 spaced centrally along its length. Each depression has a side wall 52 adapted to frictionally engage the mouth-forming portion of the container 10. Where the mouth of the container 10 is closed by an elastomeric stopper 30 and a metallic band 31 as described above, the side wall 52 of the carrier strip frictionally engages the metallic band 31 as shown in FIG. 7. Each depression has a closed end wall 53. The closed end wall prevents contact with the closure 30 during handling of the batching strip 50. Each end wall 53 may have a stepped central portion 53a to provide a peripheral seating surface 53b and to prevent the portion 53a from contacting the surface of the container closure 30.

Where frictional engagement permits flexible carrier strips to carry the containers 10, it can be achieved by providing an interference fit between the side walls of the carrier strip and the outer diameter of the portion of the container 10 to be engaged. The thermoformed plastic strips 40 and 50 will deform at each depression 41 and 51 sufficiently to permit the insertion of members 13 and the containers 10 and will provide sufficient retentive force to retain the containers in the strip. Where the processing carrier strip 40 includes a second asymmetrical side wall portion, such as portion 43b, a projection, such as 29 of member 13, may be trapped and retained by the second asymmetrical side wall portion (see FIG. 5 and FIG. 6).

Figure 8:
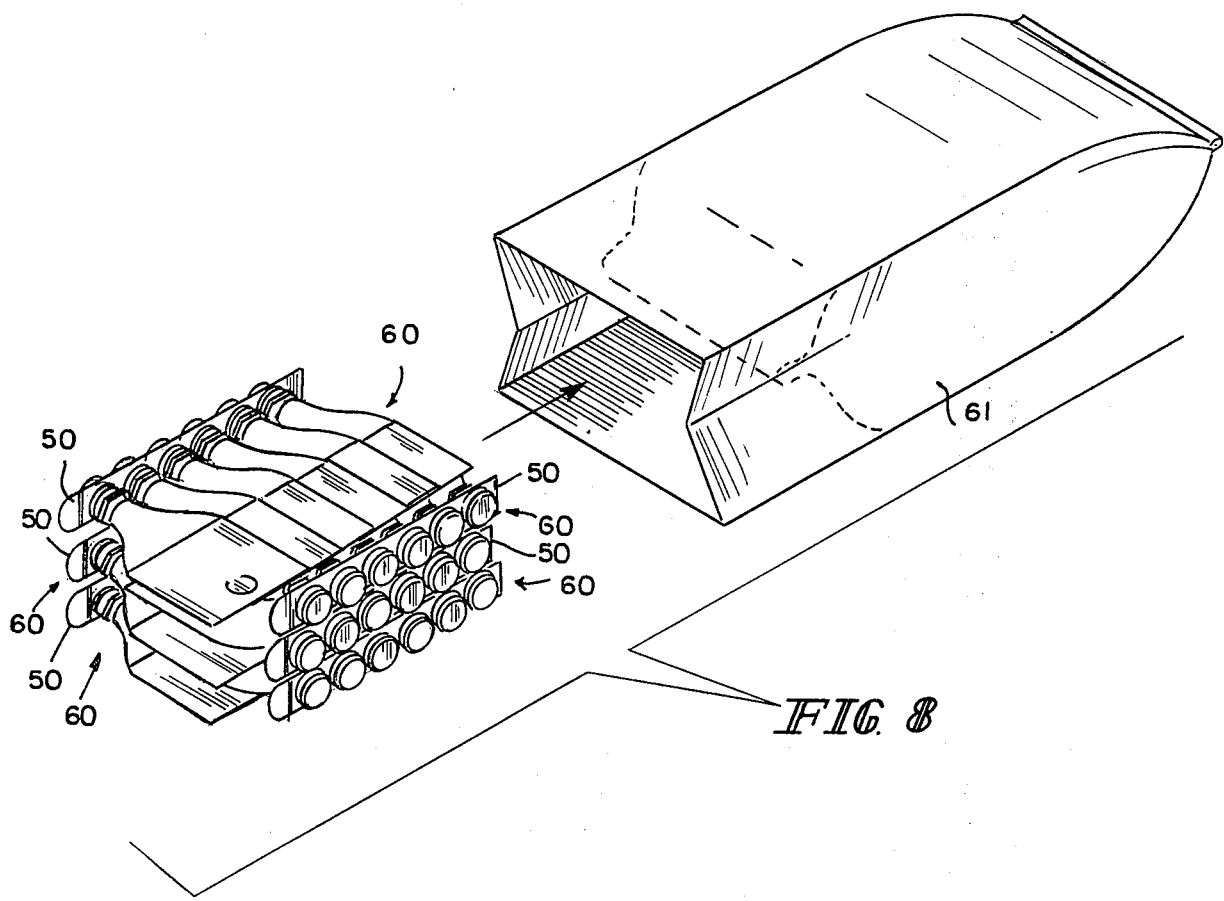
FIG. 8 illustrates the manner in which a plurality of containers are packaged in a protective storing and shipping bag.

As shown in FIG. 8, batching assemblies 60, each consisting of a carrier strip 50 carrying six bags 10, are inserted together into protective outer bag 61. The protective outer bag may be formed from a composite laminate including a layer of metallic foil and a layer of polyolefin film, which is known and commercially available. After the assemblies 60 are inserted into the bag, it is closed by folding the bag and heat-sealing it in a manner which is known. The composite film of foil and polyolefin can form a moisture barrier which protects the flexible packages 10 of dry medicine from degradation during shipment and storage. The use of the outer bag, in any event, provides additional moisture barrier protection with the film layers 11 and 12 which make up the flexible bag containers 10.

This system can be conveniently used by hospital pharmacists in the preparation of the dry medicines for intravenous administration.

Figures 10, 12:
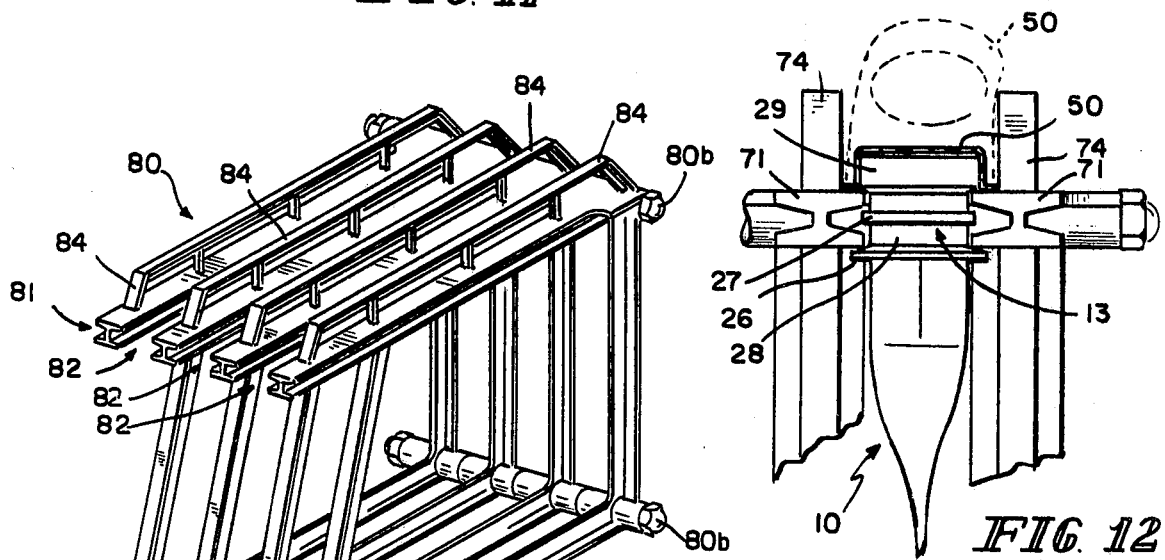
FIG. 10 is a perspective view of another pharmacy rack of this system.
FIG. 12 is a partial cross-sectional view of a plurality of containers held within the rack.
Figure 9:
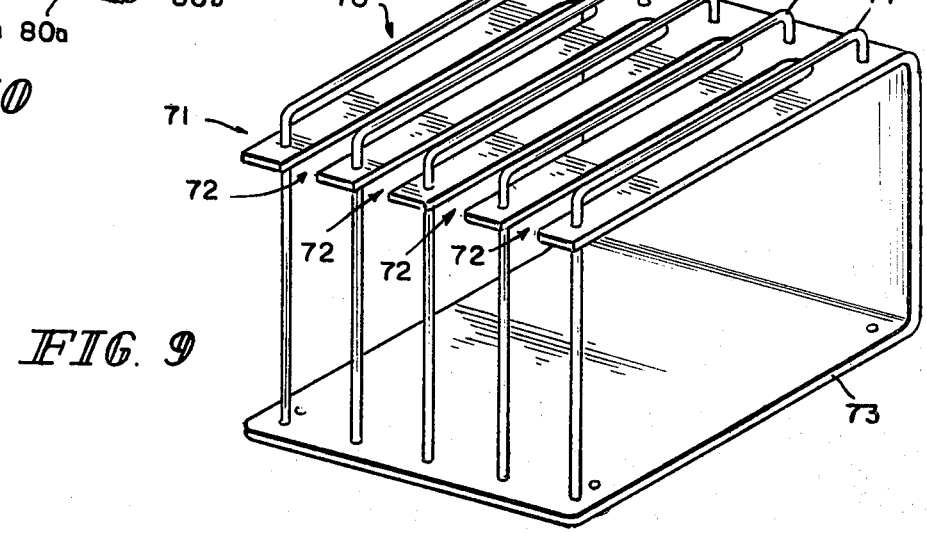
FIG. 9 is a perspective view of a pharmacy rack for use in this system.

FIGS. 9 and 10 show open racks of this system adapted to assist the pharmacist in the reconstitution of the dry medicine as a solution. Such pharmacy racks are simple and provide an open structure with the minimum of surfaces to obstruct the flow of atmosphere so that a pharmacist may use the rack within his sterile preparation chamber to prepare liquid solutions of the dry medicine.

The rack 70 of FIG. 9 is prepared for aluminum sheet metal and rod which is bent and fastened together. The rack of FIG. 10 consists of a plurality of molded elements 80a held together as a unit by fasteners 80b. Both racks include upper portions 71 and 81, respectively, forming a plurality of slots 72 and 82, respectively. Each of the slots 72 and 82 have a length of several inches in order to accommodate a plurality of containers 10. Each rack also includes a lower portion 73 and 83, respectively, forming a base for the rack. The upper portion 81 is arranged to be supported generally horizontal and several inches above the base, for example, 7 to 8 inches. One end of each of the racks 70 and 80 is open and provides obstruction-free access to the elongated slots 72 and 83. The racks include open rails 74 and 84 on each side of each of the elongated slots 72 and 82 that are supported above the upper portions 71 and 81 of the racks. As shown in FIGS. 9 and 10, the racks are largely open to permit the free circulation of sterilized air over their surfaces and over the surfaces of any containers they support during their use.

With this system, as the pharmacist wishes to prepare the dry medicines for intravenous administration, he may open the bag 61 (FIG. 8), removing the batching assemblies 60. By handling the batching carrier strips 50 of each assembly 60, he may conveniently slide the assembly 60 into the slots 72 (or 82) formed in the upper surface of the racks 70 (or 80), as shown in FIG. 11.

Figure 11:
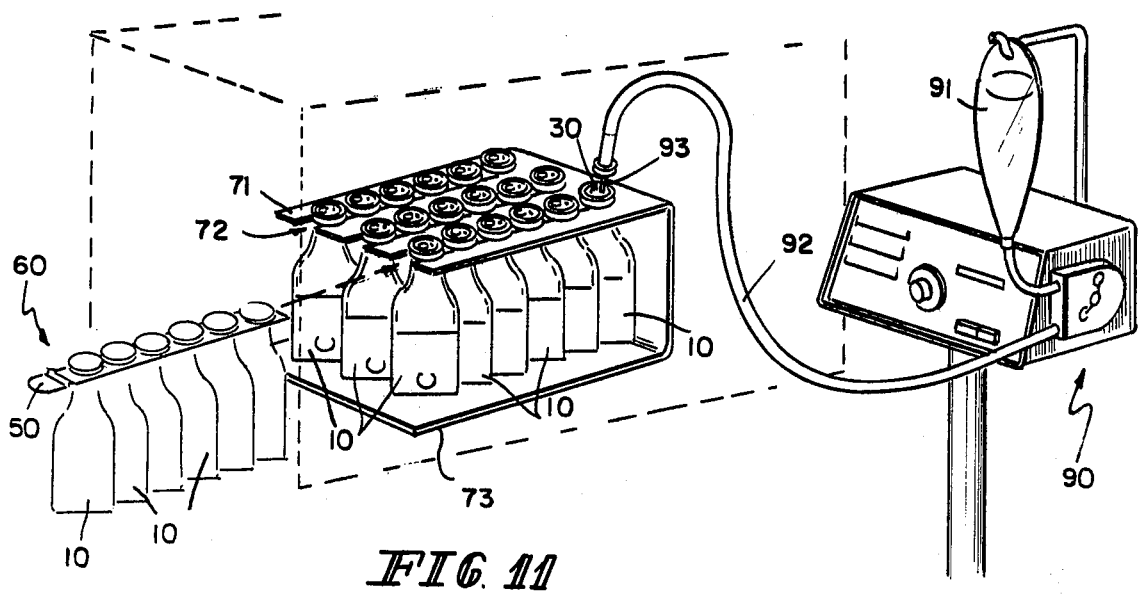
FIG. 11 is a perspective view of a system of this invention during reconstitution of the dry medicine.

As shown in FIGS. 11 and 12, the plurality of containers 10 will each be supported from a projection 27 (or 26) of their members 13 by the upper surface of the rack 71 (or 81). The projection 26 (or 27) permits the pharmacist to pull the flexible carrier strip 50 from the plurality of containers exposing their closures. As shown in FIG. 12, the rails 74 (or 84) protect the closures 30 from accidental contact, but permit removal of the carrier strip 50 and intentional access to the closures. The rails 74 or 84 have been omitted from FIG. 11 to clarify its showing of the manner in which the batch of packages 10 are supported by the rack.

In reconstituting the dry medicine, the hospital pharmacist is thus provided with a plurality of bags 10 containing the dry medicine. The individual packages 10 are provided in a plurality of assemblies 60, each containing a plurality of bags for convenient use. The bags 10 are releasably carried adjacent their opening by a flexible batching strip 50 that protects the opening from contact.

The pharmacist is further provided with a slotted support (71 or 81) for the bags that is engageable by a projection 27 (or 26) of the package located adjacent its opening. He may carry a plurality of bags by the flexible batching strip 50 and insert the entire plurality of bags 10 into the slotted support by the assembly 60. The plurality of bags is thus supported and permits the pharmacist to remove the flexible batching strip and expose the closures for each bag.

Having thus prepared a plurality of bags supported and ready for reconstitution, the pharmacist is provided with a pump which provides solution from a container 91 in controlled quantities. A flexible hose 92 and syringe 93 are connected to the output of the pump and the pharmacist is able to perforate the identified portion of the closure 30 of each bag and to deliver into its interior a controlled quantity of solution. By using the power-actuated pump to add a quantity of liquid into the bags, the use of a hand syringe is eliminated. The pharmacist may thus quickly prepare a plurality of dosages of the medicine solution ready for intravenous administration.

For example, typical containers 10 having the dimensions set forth above can carry one-gram doses of an antibiotic such as that sold by Eli Lilly and Company with their trademark KEFLIN. The hospital pharmacist can, using the system, add 50 milliliters of D5W solution (5 percent dextrose and water) to each container. The antibiotic will go into solution in the D5W; and as a result, each container 10 will carry a liquid solution of antibiotic medicine.

Figure 13:
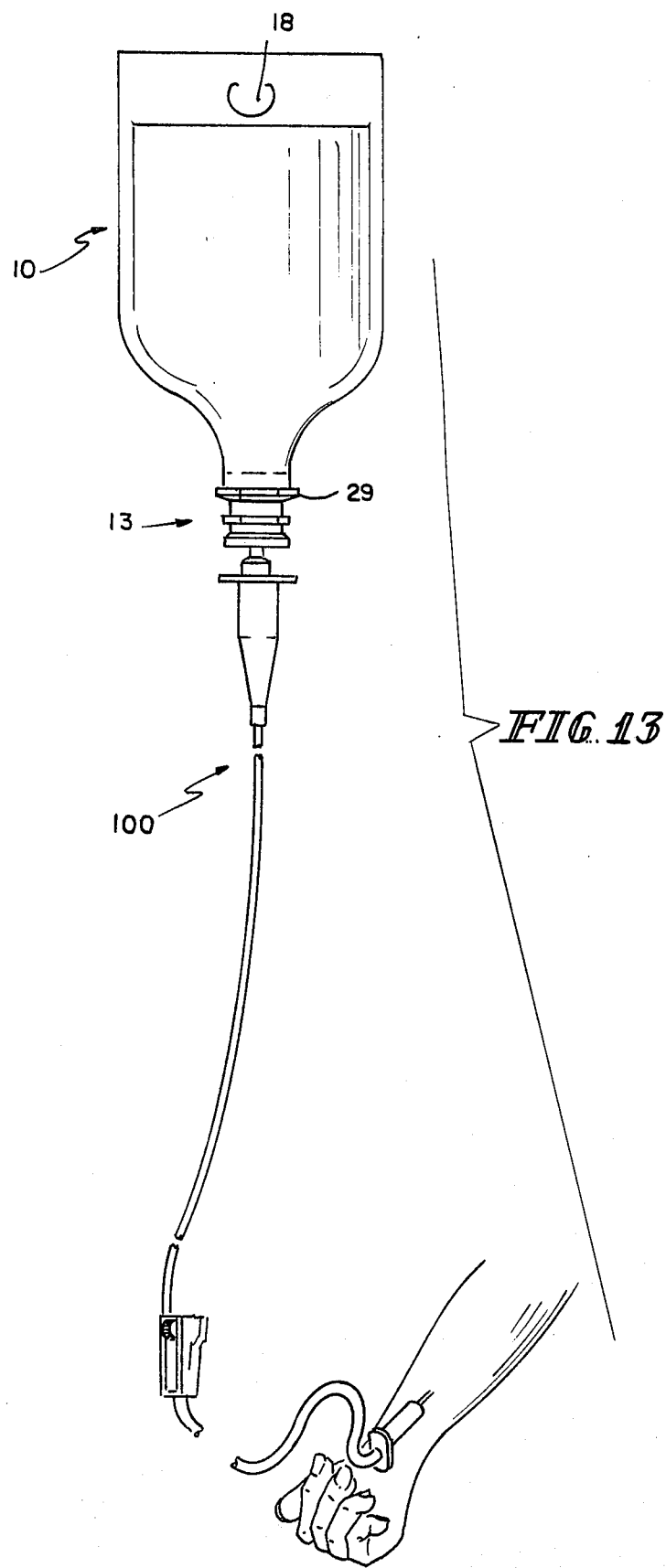
FIG. 13 is a view of the closed unit-dose system of this invention showing administration of the medicine solution to a patient.

As shown in FIG. 13, the containers 10 may then be used to administer the medicine solution directly into the veins of a patient or, for example, by its piggy-back administration with other solutions. The port-forming member 13 and its projection 29 provide convenient surfaces to handle the container 10 as the IV administration set 100 is inserted in the container 10. Because the solution is provided in the flexible bag container 10, there is no need to vent the container 10. Flexibility of the film layers 11 and 12 of the package 10 will permit the collapse of the package as it is being emptied, and the administration of a complete dosage to the patient.

Although we have shown specific embodiments of the system of our invention, other embodiments are possible without departing from the scope of the claims that follow.

What is claimed is:

1. A package for pharmaceutical materials in particulate form, comprising
   a flexible bag formed of two layers of plastic film with a portion at the one end adapted to engage a port-forming member, said two layers of plastic film being sealed at their periphery to form an enclosure, and
   a port-forming member, one end thereof defining two elongated planar side panels adopted for insertion and sealing engagement with the one portion of the bag and the other end thereof projecting from the bag and including two projecting portions, the first projecting portion being located above and adjacent the planar side panels and the second projecting portion being located intermediate the first projecting portion and uppermost end of the port-forming member, said member having a wide mouth central bore in communication with the bag enclosure.

2. A package for pharmaceutical materials in particulate form, comprising
   a flexible bag formed of two layers of plastic film having substantial portions that are sealed together to provide a panel at one end with a transverse hole in its central area and a necked portion at the other end adapted to engage a port-forming member, said two layers of plastic film being sealed at their periphery to form an enclosure, and
   a port-forming member, one end thereof defining two elongated planar side panels adopted for insertion and sealing engagement with the necked portion of the bag and the other end thereof projecting from the bag and including two projecting portions, the first projecting portion being located above and adjacent the planar side panels and the second projecting portion being located intermediate the first projecting portion and uppermost end of the port-forming member, said member having a wide mouth central bore in communication with the bag enclosure.

3. A package for pharmaceutical materials in particulate form, comprising
   a flexible bag formed of two layers of plastic film having substantial portions at one end that are sealed together to provide a planar panel at one end with a tranverse hole in its central area and a necked portion at the other end adapted to engage a port-forming member, said two layers of plastic film being sealed at their periphery to form an enclosure, and
   a port-forming member, one end thereof being eye-shaped and defined by two elongated planar side panels that intersect to form two vertices, each having an included angle of about 90° in sealed engagement with the necked portion of the bag, the other end thereof projecting from the bag and including two projecting portions, the first projecting portion being generally hexagonal in shape and located above and adjacent the planar side panels with two vertices of the hexagonal projection located immediately above the two vertices of the elongated planar side panels and the second projecting portion being located intermediate the first projecting portion and uppermost end of the port-forming member, said member having a wide mouth central bore in communication with the bag enclosure.

4. The package of claim 1 or claim 2 or claim 3 wherein the second projecting portion is in the form of a projecting annular ring with an asymmetrical portion and wherein the port-forming member includes an additional projection in the form of an annular ring located at the mouth of the port-forming member.

5. A molded plastic tubular member adapted to provide, with its central bore, the mouth of a flexible bag, comprising
a bag-engaging end and a mouth-forming end about the central bore,
said bag-engaging end being eye-shaped and formed by two outer elongated panels that meet on opposite sides of the bore at a plane through its central axis to form vertices with included angles of about 90°, each panel having a central rounded portion generally concentric with said central bore axis,
said mouth-forming portion being generally cylindrical with a plurality of projecting rings, one ring being located above and adjacent the bag-engaging end and the second ring being located above the first ring.

6. The member of claim 5 wherein the first projecting ring is in the form of a hexagon with its vertices located immediately above the vertices at the intersection of the two elongated panels, and the second projecting ring is annular except for two asymmetrical portions.

7. A system for handling dry pharmaceuticals, comprising
a plurality of containers,
each container being formed from two layers of flexible film and a port-forming member, said layers of flexible film being sealed at the periphery and to one end of the port-forming member to form a bag container for dry pharmaceuticals, said port-forming member having an inner surface forming a large mouth and bore to provide access to the interior of the bag and a sealing surface for a container closure and having an exposed outer surface defining a projection, and
a flexible plastic strip formed with a plurality of depressions, each depression having an inner surface adapted to engage and retain the projection of the exposed end of the port-forming member of each of the plurality of containers,
said system permitting the plurality of containers to be handled as an assembly.

8. The system of claim 7 wherein each depression includes a side wall and a closed end wall and said strip includes additional depressed surfaces forming a longitudinal channel from one end to the other of the elongated strip that interrupts the side walls of the plurality of depressions, each depression including a narrow channel-forming portion in its end wall and in its side wall with its side wall channel-forming portion being located within the interruption of the depression by the additional depressed surfaces that form the longitudinal channel, and wherein the side wall of each depression other than the narrow channel-forming portion engages and retains the port-forming member of bag container with the narrow channel-forming portion of each depression being free of contact with the port-forming member.

9. The strip of claim 8 wherein the engaged projection of the port-forming member is an annular ring adjacent its large mouth, and the port-forming member includes a second asymmetrical projection and wherein each depression includes a first cylindrical side wall portion adjacent its closed end and a second asymmetrical side wall portion adjacent the elongated surface of the strip that is adapted to engage and mate the asymmetrical portion of the second projection of the port-forming member of each bag container and to prevent rotation of the bag container in the elongated strip.

10. The strip of claim 9 wherein the second asymmetrical side wall portion has a cylindrical portion with the same inside diameter as the first side wall portion, except for a straight surface, and the elongated strip includes side walls at its periphery extending in the direction of and about the outer surface of the plurality of depressions.

11. A system for handling dry pharmaceuticals, comprising
a plurality of containers,
each container being formed from two layers of flexible film and a port-forming member, said layers of flexible film being sealed at the periphery and to one end of the port-forming member to form a bag container for dry pharmaceuticals, said port-forming member having an inner surface forming a bore to provide access to the interior of the bag and a sealing surface for a container closure and having an exposed outer surface defining a projection, each of said containers having a closure sealed on the sealing surface of the port-forming member, and
a flexible plastic strip formed with a plurality of centrally located sites adapted to engage and retain the projection of the exposed end of the port-forming member of each of the plurality of containers,
said system permitting the plurality of containers to be handled as an assembly.

12. A carrier strip for bag containers of dry pharmaceuticals having rigid mouth-forming members, comprising
an elongated flexible plastic strip having a plurality of cylindrical depressions spaced centrally along its length, each depression having a sidewall adapted to be frictionally engageable with the rigid mouth-forming members of the bag containers and having an end wall that is stepped to provide a peripheral end wall seating surface for the mouth-forming members and to provide a further depressed central end wall portion that does not contact the enclosed end of the rigid mouth-forming member.

13. A carrier strip for handling empty bag containers during processing, comprising
an elongated flexible strip having a plurality of depressions spaced centrally along its length, each depression including a side wall and a closed end wall, said strip including additional depressed surfaces forming a longitudinal channel from one end to the other of the elongated strip that interrupts the side walls forming the plurality of depressions, each depression including a narrow channel-forming portion in its end wall and in its side wall with its side wall channel-forming portion being located within the interruption of the depression by the additional depressed surfaces that form the longitudinal channel, the side wall of each depression other than the narrow channel-forming portion being adapted to engage and retain a port-forming member of bag container with the narrow channel-forming portion of each depression being free of contact with the port-forming member.

14. The carrier strip of claim 13 wherein each depression includes a first cylindrical side wall portion adjacent its closed end and a second side wall portion adjacent the elongated surface of the strip that includes an asymmetrical side wall section adapted to engage an asymmetrical portion of the port-forming member of each bag container and to prevent rotation of the bag container in the elongated strip.

15. The carrier strip of claim 14 wherein the second side wall portion has a cylindrical portion with the same inside diameter as the first side wall portion, except for its asymmetrical surface, and the elongated strip includes side walls at its periphery extending in the direction of and about the outer surface of the plurality of depressions.

16. A batching assembly for processing a plurality of bag containers, comprising a plurality of flexible bag containers, each flexible bag being formed of two layers of plastic film, said two layers of plastic film being sealed at their periphery to form an enclosure at one end and being formed at the other end to provide a necked portion adapted to engage a port-forming member, and a port-forming member, one end thereof defining two elongated planar side panels adapted for insertion and sealing engagement with the necked portion of the bag and the other end thereof projecting from the bag and including two projecting annular ring portions, the first projecting annular ring defining the end of the member and the second projecting annular ring being located intermediate the first projecting portion and the bag, said member having a wide mouth central bore in communication with the bag enclosure, and a processing carrier strip for the plurality of bag containers, comprising an enlongated flexible strip having a plurality of depressions spaced centrally along its length, each depression including a side wall and a closed end wall, said strip including additional depressed surfaces forming a longitudinal channel from one end to the other of the elongated strip that interrupts the side walls forming the plurality of depressions, each depression including a narrow channel-forming portion in its end wall and in its side wall with its side wall channel-forming portion being located within the interruption of the depression by the additional depressed surfaces that form the longitudinal channel, said plurality of flexible bag containers having the exposed ends of its port-forming members retained within the depressions of the processing carrier strip, the side wall of each depression other than the narrow channel-forming portion being adapted to engage and retain the port-forming members of the bag container with the narrow channel-forming portion of each depression being free of contact with the port-forming member.

17. The system of claim 16 wherein the second projecting annular ring portions of the port-forming members of the bag containers has a straight peripheral portion, and each depression includes a first cylindrical side wall portion adjacent its closed end and a second side wall portion adjacent the elongated surface of the strip that includes a straight side wall section adapted to engage the straight portion of the second projecting annular ring of the port-forming member of each bag container and to prevent rotation of the bag containers in the elongated strip.

18. The sytem of claim 17 wherein the first projecting annular ring portions of the port-forming members of the bag containers have been captured in the first cylindrical side wall portions of the carrier strip by the straight side wall of the second side wall portion.

19. A batching assembly for processing a plurality of packages of pharmaceutical materials in particulate form, comprising a plurality of flexible bags, each flexible bag being formed of two layers of plastic film, said two layers of plastic film being sealed at their periphery to form an enclosure at one end and a necked portion at the other end adapted to engage a port-forming member, and a port-forming member, one end thereof defining two elongated planar side panels adapted for insertion and sealing engagement with the necked portion of the bag and the other end thereof projecting from the bag and including a projecting annular ring portion defining the end of the member and providing a surface engageable by a bag closure, said member having a wide mouth central bore in communication with the bag enclosure and a closure sealing the mouth of the bore, a batching carrier strip for the plurality of bag containers comprising an elongated flexible plastic strip having a plurality of cylindrical depressions spaced centrally along its length, each depression having a side wall adapted to be frictionally engageable with the port-forming members of the bag containers and having an end wall that is stepped to provide a peripheral end wall seating surface for the port-forming members and to provide a central end wall portion that is further depressed so that it does not contact the closure of the port-forming member, said plurality of flexible bags having their port-forming members frictionally retained within the depressions of the batching carrier strip.

20. A method for reconstituting dry pharmaceuticals, comprising providing a plurality of bags containing a dry pharmaceutical releasably carried adjacent their opening by a flexible strip that protects the opening from contact, providing a slotted support for the bags that is engageable by a projecting surface of the bag located adjacent its opening, carrying the plurality of bags by the flexible strip and inserting the entire plurality of bags into the slot of the support while carrying the projecting surface of the bag above the support, removing the flexible strip to expose the opening of the bag, and pumping a quantity of liquid into the bags to place the dry pharmaceuticals in the plurality of bags in solution in said liquid.

21. The system of claim 20 wherein the plurality of bags are sealed at their opening by elastomeric stoppers, the flexible strip protects the elastomeric stoppers from contact and the stoppers are exposed upon its removal, the elastomeric stoppers are pierced by a hollow needle connected with power-operated pump, and the liquid is forced by said pump in an automatically predetermined quantity into each bag for reconstitution of the dry pharmaceutical.

22. The method of claim 20 or claim 21 including the additional steps of inserting an intravenous administration set into the opening of the bag, hanging the bag so that gravity will urge the flow of medicine solution from the bag and infusing the pharmaceutical solution into the vein of a patient.

23. A method for reconstituting and administering dry pharmaceuticals, comprising providing a plurality of bags containing a dry pharmaceutical releasably carried adjacent their opening by a flexible strip that protects the opening from contact, providing a slotted support for the bags that is engageable by a projecting surface of the bag located adjacent its opening, carrying the plurality of bags by the flexible strip and inserting the entire plurality of bags into the slot of the support while carrying the projecting surface of the bag above the support, removing the flexible strip to expose the opening of the bag, pumping a quantity of liquid into the bags to place the dry pharmaceuticals in the plurality of bags in solution in said liquid, and withdrawing the pharmaceutical solution through the opening and infusing the solution into the vein of a patient.

24. The system of claim 23 wherein the plurality of bags are sealed at their opening by elastomeric stoppers, the flexible strip protects the elastomeric stoppers from contact and the stoppers are exposed upon its removal, the elastomeric stoppers are pierced by a hollow needle connected with power-operated pump, the liquid is forced by said pump in an automatically predetermined quantity into each bag for reconstitution of the dry pharmaceutical, and the stopper is pierced again by a standard intravenous administration set for withdrawal of the pharmaceutical solution and its infusion into the vien of a patient under gravity.

25. A pharmacy rack for use in reconstitution of dry pharmaceuticals, comprising an upper portion forming an elongated slot having a length of several inches and a lower portion forming a base, said rack being adopted to rest on its base with its upper portion supported generally horizontal and several inches above the base and with an obstruction-free access to the elongated slot, and a pair of open rails on each side of the slot that project above the upper portion of the rack, said upper and lower portions of the rack being open to permit a free circulation of atmosphere past the rack.

26. The rack of claim 25 formed from a plurality of individual identical molded plastic sections, each plastic section including an upper portion formed to provide one side of an elongated slot when assembled with another section, a lower base-forming portion and a supporting portion between the upper and lower portions, each plastic section including generally adjacent the ends of its lower portion and at one end of its upper portion bosses adapted for engagement and fastening with other sections.

27. The rack of claim 26 wherein the bosses have central bores to permit the individual sections to be bolted together, said bosses at the lower portion being adapted to provide a base.

28. A system for use in reconstitution of dry pharmaceuticals, comprising a rack having an upper surface forming an elongated slot and a lower surface forming a base, said rack being adopted to rest on its base and support the upper slot-forming surfaces generally horizontal and several inches above the base and to provide an obstruction-free access to the slot and a structure generally open to circulation of atmosphere, a plurality of containers supported in the slot by the upper surface of the rack, each container being formed from two layers of flexible film and a rigid member having an exposed port-forming portion, said layers of flexible film being sealed at the periphery and to one end of the port-forming member to form a bag container for dry pharmaceuticals, the exposed port-forming portion of the rigid member having an inner surface forming an opening to provide access to the interior of the bag and a sealing surface for a closure, the exposed port-forming portion further having an outer surface defining a projection with said projection being engaged and supported by the upper slot-forming surface of the rack, each of said containers having a closure within the opening and sealed at a sealing surface of the mouth of the port-forming member, a flexible plastic strip formed with a plurality of centrally located sites adapted to engage and retain the exposed end of the rigid members of the bag containers, the closure of each container being covered and protected from contamination by said strip, said system providing the plurality of bag containers for filling with liquid.

29. The system of claim 28 wherein the exposed end of the rigid members of each bag include a plurality of projections, and the centrally located sites of the flexible plastic strip are a plurality of depressions, said depressions and projections of said rigid members being frictionally engaged.

* * * * *